United States Patent
Khan et al.

(10) Patent No.: US 9,459,241 B2
(45) Date of Patent: Oct. 4, 2016

(54) PRINTABLE OXYGEN SENSING COMPOSITION

(75) Inventors: Sarfaraz Akhtar Khan, Kent (GB); Michael William Leonard, Kent (GB); Robert Lines, Kent (GB)

(73) Assignee: Sun Chemical B.V., Weesp (NL)

( * ) Notice: Subject to any disclaimer, the term of this patent is extended or adjusted under 35 U.S.C. 154(b) by 520 days.

(21) Appl. No.: 12/679,386

(22) PCT Filed: Sep. 18, 2008

(86) PCT No.: PCT/GB2008/003189
§ 371 (c)(1),
(2), (4) Date: Mar. 22, 2010

(87) PCT Pub. No.: WO2009/037477
PCT Pub. Date: Mar. 26, 2009

(65) Prior Publication Data
US 2010/0221468 A1    Sep. 2, 2010

(30) Foreign Application Priority Data

Sep. 21, 2007   (GB) .................................. 0718509.3

(51) Int. Cl.
| | |
|---|---|
| *C08L 81/00* | (2006.01) |
| *C08L 85/02* | (2006.01) |
| *B32B 33/00* | (2006.01) |
| *B32B 1/00* | (2006.01) |
| *G01N 31/22* | (2006.01) |
| *C07D 471/04* | (2006.01) |
| *G01N 21/77* | (2006.01) |

(52) U.S. Cl.
CPC ........... *G01N 31/225* (2013.01); *C07D 471/04* (2013.01); *G01N 2021/7786* (2013.01); *Y10T 428/1334* (2015.01); *Y10T 428/24802* (2015.01)

(58) Field of Classification Search
CPC ..... C07D 471/04; C09B 43/40; C09B 62/09; C09B 62/002; C09B 62/02; B32B 27/00; B32B 33/00; B32B 1/00; C09D 11/326; G01N 2021/7786; G01N 31/225; Y10T 428/1334; Y10T 428/24802; C08F 216/1466; C08F 2216/1475; C08F 290/062; C08F 297/00; C08F 297/02; C08F 8/36
USPC .................. 428/36.7, 35.2, 195.1; 524/610; 106/31.48
See application file for complete search history.

(56) References Cited

U.S. PATENT DOCUMENTS

| | | | |
|---|---|---|---|
| 4,349,509 A | 9/1982 | Yoshikawa et al. | |
| 5,030,420 A | 7/1991 | Bacon et al. | |
| 6,022,908 A | 2/2000 | Ma et al. | |
| 6,306,661 B1 | 10/2001 | Lakowicz et al. | |
| 6,673,500 B1 | 1/2004 | Patel et al. | |
| 6,689,438 B2 | 2/2004 | Kennedy et al. | |
| 7,368,153 B2 * | 5/2008 | Barmore et al. | ............. 428/36.7 |
| 2004/0131806 A1 | 7/2004 | Barmore et al. | |
| 2006/0228804 A1 | 10/2006 | Xu et al. | |
| 2006/0235177 A1 * | 10/2006 | Ikegami et al. | ............. 526/287 |
| 2006/0257094 A1 | 11/2006 | McEvoy et al. | |
| 2009/0226948 A1 | 9/2009 | Reichert et al. | |

FOREIGN PATENT DOCUMENTS

| | | |
|---|---|---|
| CN | 1767945 | 5/2006 |
| DE | 30 25 264 | 1/1981 |
| EP | 0692528 | 1/1996 |
| GB | 2132348 A | 7/1984 |
| JP | S 62148580 | 7/1987 |
| JP | H01280242 | 11/1989 |
| JP | 11-343440 H | 12/1999 |
| JP | 2000-154343 A | 6/2000 |
| JP | 2005048137 | 2/2005 |
| JP | 2006052400 A | 2/2006 |
| JP | 2006-508872 A | 3/2006 |
| WO | WO-9803865 A1 | 1/1998 |
| WO | WO 99/40424 | 8/1999 |
| WO | WO-0163264 A1 | 8/2001 |
| WO | WO 2004/052644 | 6/2004 |
| WO | WO 2004/099270 | 11/2004 |
| WO | WO-2006015961 A2 | 2/2006 |
| WO | 2007088149 A1 | 8/2007 |
| WO | WO 2007088149 | * 8/2007 |

OTHER PUBLICATIONS

International Search Report, mailed Dec. 5, 2008.
Korean Office Action dated Jun. 27, 2014 in connection with Korean Application No. 10-2010-7008707.
Office Action issued on Jun. 9, 2014 in connection with Japanese Patent Application No. 2010-525433 (with English translation).
International Preliminary Report on Patentability and Written Opinion for International Application No. PCT/GB2008/003189, dated Mar. 24, 2010.
UK Intellectual Property Office Search Report for Application No. GB0718509.3 dated Feb. 8, 2008.
Japanese Office Action issued in Japanese Application No. 2014-206286, dated Nov. 30, 2015 (with English Language Translation).

* cited by examiner

*Primary Examiner* — Yan Lan

(74) *Attorney, Agent, or Firm* — Charles C. Achkar; Ostrolenk Faber LLP

(57) ABSTRACT

An ink composition comprising an oxygen sensitive dye capable of fluorescing in a manner proportional to oxygen content; and a polymer matrix for the dye, the polymer matrix having units with pendant sulphonic acid or phosphonic acid groups or salts or esters of such groups, can be used with an appropriate meter to measure the oxygen content of packages in a non-invasive manner.

15 Claims, No Drawings

PRINTABLE OXYGEN SENSING COMPOSITION

RELATED APPLICATIONS

This application is the U.S. National Stage of International Application Number PCT/GB2008/003189, filed 18 Sep. 2008, which claims benefit of priority to GB-0718509.3, filed 21 Sep. 2007, the specification of which is incorporated by reference herein.

The present invention relates to an oxygen sensing composition capable of being printed by a variety of printing techniques.

The development of measurement systems to detect oxygen content is of immense importance in a wide variety of applications. Oxygen can severely reduce the life of a product, causing significant spoilage. Foods, beverages, pharmaceuticals and a variety of other products when exposed to oxygen may, over time, experience diminishing shelf life.

Currently methods exist whereby low oxygen levels can be maintained. Manufacturers of packaged products have developed packaging materials and systems to achieve this, e.g. packaging materials may contain an oxygen scavenger within a low oxygen modified atmosphere package (MAP) or a vacuum package (VP). The oxygen content within the package can be measured by analysis of the headspace within the package and a number of methods are currently available, e.g. invasive and non-invasive headspace analyzers. Mocon Inc and Dansensor Inc. have developed invasive headspace analyzers. Unfortunately, these necessarily require a probe device to penetrate the package whose oxygen content is to be determined, thus destroying the integrity of the package, and adding to increased costs and waste. Moreover, patently not every package can be tested in this way, and the device can only be applied to samples, from which inferences may be made as to the oxygen content of the untested packages.

There has, therefore, been a concerted effort by manufacturers of packaged products and manufacturers of gas analyzers to develop non-invasive headspace analyzers. Although a great deal of prior art exists, not all of the problems have been solved, giving rise to stiff competition. In general, the approach adopted has been to develop a printable oxygen sensing coating comprising a metal complex immobilized in a polymer matrix, this coating being printed onto a substrate. The printed coating may then be irradiated, e.g. with a blue LED, and the resulting fluorescence will give an indication of the amount of oxygen detected by the coating. There are two common ways of using this to determine oxygen content. One relies on the intensity of the measured fluorescence and the other measures the decay time of the fluorescence. The latter is considered more accurate as intensity can vary depending on the type of packaging used.

US 2006/0257094 A1 describes an optical sensing film with a gas analyzer to confirm the integrity of the package in a non-invasive and non-destructive manner. The gas sensor is produced from a solution which is printable or coatable, the oxygen sensing component of the solution being tris(4,7-diphenyl-1-10-phenanthroline)-ruthenium (II) chloride immobilized in a porous hybrid sol gel. The dye is entrapped within the porous matrix giving the sensor its desired properties. U.S. Pat. No. 6,689,438 B2 describes an oxygen detection system for a solid article; the preferred oxygen indicator being a palladium complex, immobilized in cellulose acetate butyrate (CAB), polystyrene (PS) or poly(methyl methacrylate) (PMMA) giving a film thickness of 15-20 μm. In some cases the oxygen sensitivity was further increased by addition of plasticizers, or tributyl phosphate. U.S. Pat. No. 5,030,420 describes a method and apparatus for determining the presence of oxygen in a gaseous or liquid environment, wherein the luminescence oxygen sensitive material, tris (4,7-diphenyl-1,10-phenanthroline)-ruthenium (II) perchlorate is immobilized in a silicon rubber. The immobilization of the ruthenium dye into the carrier matrix from a suitable organic solution is achieved either by diffusion, mixing before final polymerization, and ionic or covalent binding. The carrier matrix is selected from Plexiglas, polyvinyl chloride, silicone rubber, natural rubber, polycarbonate, Teflon, polystyrene, polyvinylidene fluoride, poly(tetrafluoroethylene propylene) and anion and cation exchange resins. The polymer is protected further from the environment by over coating it with an oxygen permeable solvent resistant polymer such as Teflon. US 2006/0228804 A1 discloses a modified ruthenium complex luminescence dye for oxygen sensing, the dye being modified by the attachment of long chain hydrophobic groups to the ligands of the ruthenium dye via covalent bonding, thus allowing the dye to be soluble in non-polar solvents e.g. toluene and allow it to be immobilized in non-polar polymers e.g. polystyrene.

None of the prior art materials has been wholly successful. Thus, for example, the sol-gel based coatings are liable to shrinkage and collapse of the porous structure, resulting in poor oxygen permeation; while those based on carboxylic polymers do not give sufficient accuracy.

We have now surprisingly found that the incorporation of sulphonic acid or phosphonic acid (or equivalent salt or ester) groups in the polymer used as support for the oxygen sensing compound can enable these disadvantages to be overcome. As a result, we have developed an ink which can produce printable oxygen-sensing elements.

Oxysense® has commercialized a non-invasive optical sensor for oxygen detection based on fluorescence lifetime/decay of a ruthenium dye complex. WO 01/63264 A1 discloses the use of fluoridated silicon polymer as an embedding medium for the Ru dye complex, and the resulting embedded complex may be used as the sensor in an Oxysense system. The embedded Ru complex is formed as a dot within a porous glass, bead like structure. The glass beads known as 'OxyDots' are made and each batch is calibrated. Each dot has to be attached individually to a package. Clearly, this limits the use of the oxygen analyser to laboratory rather than mass food packaging measurements. By developing an ink which can be used to print the dots at consistent film weights, we eliminate the need for individual attachment and open up the possibility of mass printed dots, which are thus suitable for food packaging applications.

Thus, the present invention consists in an ink composition comprising: an oxygen sensitive dye capable of fluorescing in a manner proportional to oxygen content; and a polymer matrix for the dye, characterised in that the polymer matrix comprises units having pendant sulphonic acid or phosphonic acid groups or salts or esters of such groups.

The invention also provides, in another aspect, a low oxygen modified atmosphere or vacuum packaged material having on the inside of the package an oxygen sensor, characterised in that the oxygen sensor is an ink composition according to the present invention.

There is no particular restriction on the nature of the oxygen sensitive dye used in the present invention, and any such dye used in conventional compositions may equally be used here. The dye should be capable of fluorescing in a manner proportional to the oxygen content of the atmosphere surrounding it. Thus, for example, the intensity of fluorescence may be proportional to oxygen content, or, and more preferably, the decay of fluorescence may be proportional to oxygen content, as in the prior art. Examples of such dyes include: ruthenium(II), osmium(II), iridium(III), rhodium(III) and chromium ions with ligands, especially α-diimine ligands, such as 2,2'-bipyridine, 1,10-phenanthroline, 4,7-diphenyl-1-10-phenanthroline, 4,7-disulphonated-diphenyl-1,10-phenanthroline, 5-bromo-1,10-phenanthroline, 5-chloro-1,10-phenanthroline and other diimine ligands. Examples of these complexes include tris(2,2'-bipyridine)ruthenium(II) salts, tris(1,10-phenanthroline)ruthenium(II) salts and tris(4,7-diphenyl-1-10-phenanthroline) ruthenium (II) salts, especially the chloride described above. Other possible systems include similar palladium(II) and platinum(II) complexes with α-diimine ligands Of these dyes, we prefer the tris(4,7-diphenyl-1-10-phenanthroline) ruthenium (II) salts, especially the chloride.

One or more of these dyes is then immobilised in a polymer matrix having pendant sulphonic or phosphonic groups (the term "sulphonic groups" being used herein to mean sulphonic acid groups or ester or salt groups derived from such sulphonic acid groups and the term "phosphonic groups" being used correspondingly to mean phosphonic acid groups or ester or salt groups derived from such phosphonic acid groups). The polymer used in the present invention may be prepared by copolymerising a first ethylenically unsaturated compound, e.g. an acrylic monomer or oligomer, with a second ethylenically unsaturated compound, this one containing one or more sulphonic or phosphonic groups. Provided the acrylic monomer or oligomer and the sulphonic or phosphonic group-containing compound are copolymerisable, there is no particular restriction on them.

Examples of suitable acrylic monomers include: acrylic acid; methacrylic acid; alkyl (preferably $C_1$-$C_6$ alkyl) acrylates, such as methyl acrylate, ethyl acrylate, propyl acrylate, isopropyl acrylate, butyl acrylate, isobutyl acrylate, sec-butyl acrylate, t-butyl acrylate, pentyl acrylate, isopentyl acrylate, hexyl acrylate and isohexyl acrylate; alkyl (preferably $C_1$-$C_6$ alkyl) methacrylates, such as methyl methacrylate, ethyl methacrylate, propyl methacrylate, isopropyl methacrylate, butyl methacrylate, isobutyl methacrylate, sec-butyl methacrylate, t-butyl methacrylate, pentyl methacrylate, isopentyl methacrylate, hexyl methacrylate and isohexyl methacrylate; aryl and aralkyl acrylates and methacrylates, such as phenyl acrylate, phenyl methacrylate, benzyl acrylate, benzyl methacrylate, naphthyl acrylate, and naphthyl methacrylate. Of these, we particularly prefer the alkyl acrylates, and especially butyl acrylate. Other monomers which may be used as the first ethylenically unsaturated compound include styrene, vinyltoluene, t-butylstyrene, methylstyrene and vinyl acetate. Oligomers which may be used as the first ethylenically unsaturated compound include polyethylene glycol (meth)acrylates, polypropylene glycol (meth)acrylates, polyester oligomer acrylates and poly ε-caprolactone (meth)acrylates. Polymers such as polyurethanes, polyesters, and polyethers may also be copolymerised with a sulphonic or phosphonic group containing compound.

Examples of suitable sulphonic or phosphonic group containing compounds include those of formula (I):

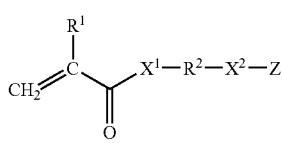

(I)

where:
$R^1$ represents a hydrogen atom or a $C_1$-$C_6$ alkyl group;
$X^1$ represents an oxygen atom, a group of formula —NH— or an alkylene group;
$R^2$ represents an alkylene group, an arylene group, a group -A-B- (where one of A and B is an alkylene group and the other of A and B is an arylene group, an oxyalkylene group or an alkyleneoxy group;
$X^2$ represents an oxygen atom or an alkylene group; and
Z represents a group of formula (II) or (III):

(II)

(III)

in which $R^3$ represents a hydroxy group, an alkyl group, an arylalkyl group, an alkoxy group or a group of formula (IV):

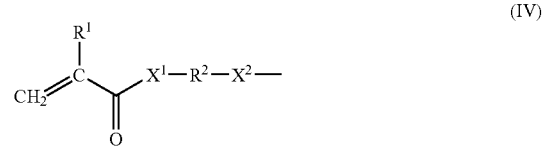

(IV)

in which $R^1$, $X^1$, $R^2$ and $X^2$ are as defined above;
and salts and esters thereof.

Examples of suitable sulphonic group containing compounds include: acrylic group containing compounds, e.g. compounds of formula (V):

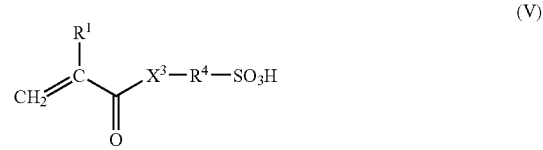

(V)

in which:
$R^1$ is as defined above;
$X^3$ represents an oxygen atom or a group of formula —NH—; and
$R^4$ represents an alkylene group, an arylene group, an oxyalkylene group or an alkyleneoxy group;
and salts and esters thereof.

Examples of suitable phosphonic group containing compounds include acrylic group-containing compounds, e.g. compounds of formula (VI):

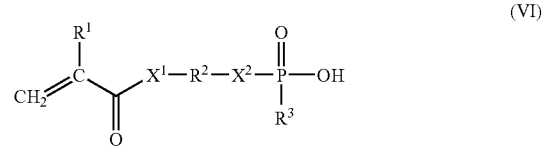

(VI)

in which $R^1$, $R^2$, $R^3$, $X^1$ and $X^2$ are as defined above.

Where $R^1$ or $R^3$ represents an alkyl group, this preferably has from 1 to 6 carbon atoms, and may be a straight or branched chain group. Examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which the ethyl and methyl, especially the methyl, groups are most preferred.

Where $R^2$, $X^1$, $X^2$, A or B represents an alkylene group, this is a bivalent saturated aliphatic hydrocarbon group, preferably having from 1 to 3 carbon atoms, and examples include the methylene, ethylene, propylene, trimethylene, tetramethylene, ethylethylene, pentamethylene and hexamethylene groups, of which the methylene, ethylene and trimethylene groups are preferred.

Where $R^2$, A or B represents an arylene group, this is a bivalent aromatic carbocyclic group which may substituted or unsubstituted. Examples include the phenylene, α-naphthylene and β-naphthylene groups and substituted analogues thereof.

Where $R^2$ represents an alkyleneoxy or oxyalkylene group, this preferably has from 1 to 6 carbon atoms, and may be a straight or branched chain group. It is a bivalent group attached at one end via an oxygen atom (the "oxy") and at the other through a carbon atom (of the "alkylene" part). Examples include the methyleneoxy, oxymethylene, ethyleneoxy, oxyethylene, propyleneoxy, oxypropylene, trimethyleneoxy, oxytrimethylene, tetramethyleneoxy, oxytetramethylene, pentyleneoxy, oxypentylene, hexyleneoxy and oxyhexylene groups, of which we prefer those groups having from 1 to 4 carbon atoms.

Preferred compounds of formula (I) are those in which $R^1$ represents a hydrogen atom or a methyl group and $R^2$ represents an alkylene group having from 2 to 4 carbon atoms, more especially those in which X represents a group of formula —NH—. Of these, the most preferred compound is 2-acrylamido-2-methyl-1-propanesulphonic acid and salts thereof. Examples of suitable salts include the $Li^+$, $Na^+$, $K^+$, $Mg^{++}$, $Ca^{++}$, $Al^{+++}$, $NH4^+$, monoalkylammonium, dialkylammonium, trialkylammonium and quaternary ammonium salts (and the aryl and aralkyl analogues thereof).

Alternatively, a pre-formed polymer containing pendant reactive groups, such as carboxylic acid groups, may be reacted with a compound containing a sulphonic or phosphonic acid, salt or ester group. In this case, the sulphonic or phosphonic compound has the formula (VII):

$$HO-X^1-R^2-X^2-Z \qquad (VII)$$

or (VIII):

$$H_2N-X^1-R^2R-X^2-Z \qquad (VIII)$$

in which $R^1$, $R^2$, $X^1$, $X^2$ and Z are as defined above.

Examples of acrylic sulphonic acid and phosphonic acid monomers for free radical polymerization reactions include 2-acrylamido-2-methyl-1-propanesulphonic acid, 3-sulphopropyl acrylate potassium salt, 3-sulphopropyl methacrylate potassium salt, ethylene glycol methacrylate phosphate, and bis[2-(methacryloyloxy)ethyl]phosphate. Examples of sulphonic acid and phosphonic acid monomers for ester and amide bond formation include 3-hydroxy-1-propanesulphonic acid, 3-amino-1-propanesulphonic acid, 2-hydroxyethyl phosphonic acid, and 3-aminopropylphosphonic acid.

The proportion of units derived from the sulphonic or phosphonic group containing compound may vary over a wide range. We prefer that these units should comprise less than 50% by weight of the sulphonic or phosphonic group-containing polymer, for example from 5 to 20, more preferably from 7 to 15% by weight of that polymer.

The polymers may be prepared by techniques well known to those skilled in the art.

Although we do not wish to be limited by any theory, we believe that the initial complex comprising the oxygen-sensitive dye undergoes an ion exchange with the sulphonic groups of the polymer, thus bonding the dye and polymer, e.g. as follows:

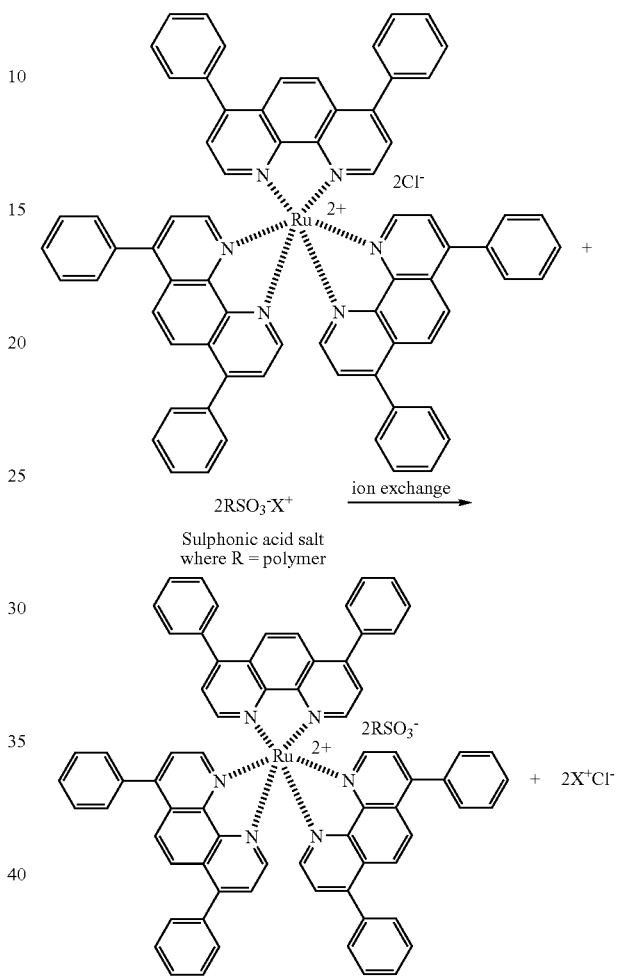

Sulphonic acid salt where R = polymer

In addition to the materials described above, the composition may contain other components to render the composition printable. Such other components may include, for example, resins, solvents (e.g. isopropanol), release agents (e.g. polydimethylsiloxane) and binders [such as polyvinyl butyral (PVB), nitrocellulose, polyurethanes (PU), polyesters, cellulose acetyl propionate (CAP), polyacrylates, polyamides and polyvinyl alcohol].

The compositions may be printed using many conventional printing techniques, including the gravure, flexo, inkjet, letterpress, screen and offset printing techniques. The compositions of the present invention will, of course, be formulated in accordance with the specific requirements of the printing technique used, as is well known in the art.

There is no restriction on the nature of the substrate on which the composition of the present invention is printed. Examples include paper, cardboard, cellophane and various plastics films. Any plastic materials commonly used in the industry, especially for food wrapping, may be used as the plastics film. Examples of such materials include synthetic and semi-synthetic organic polymers, such as cellulose acetate, cellulose acetate butyrate (CAB), cellophane, polyvinyl chloride (PVC), polyvinyl fluoride, polyvinylidene chloride (PVDC), polyethylene, polypropylene (PP), polyamides, polyesters, polyphenylene oxide, polyethylene terephthalate (PET), polybutylene terephthalate (PBT), polymethyl methacrylate, poly(methyl pentene (TPX), polyvinyl acetal, polystyrene, acrylonitrile-butadiene-styrene (ABS), acrylonitrile-styrene-acrylate (ASA), polycarbonate, polystyrene, polyether sulphone, polyether ketones, polyimides, and copolymers and/or mixtures thereof. If desired, films made from any of these polymers may be coated with coating materials well known in the art, and/or may be laminated to a film or films made of the same or different polymers. Further examples of such plastic materials may be found in standard reference texts, such as "Plastic Films", $3^{rd}$ Edition, by J. H. Briston, published by Longman Group in 1989.

The composition of the present invention is preferably formulated as an ink with a suitable solvent or mixture of solvents. The nature of the solvent will vary, depending principally on the nature of the printing process in which it is to be used. For example, if the ink is to be printed by a flexo gravure or inkjet process, suitable inks would include: ethyl, isopropyl and n-propyl alcohols; ethyl, isopropyl and n-propyl acetates; aliphatic and aromatic hydrocarbon solvents; glycol ethers; and water. However, if the ink is to be used in a litho or letterpress process, suitable solvents might include petroleum distillates and fatty acid esters.

The exact amounts of the individual components of the ink may vary over a wide range, depending on the printing process to be employed and other factors, such as are well known to those skilled in the art. By way of example, the polymer may comprise from 20 to 35% by weight, the dye around 0.1 to 1% and additional polymers [e.g. poly (dimethylsiloxane)-graft-polyacrylates (PDMS) to increase the oxygen transmission rate and to aid film forming] from 10 to 25% of the total ink, the solvent and other additives (if any) being the balance. After drying, the thickness of the ink layer is preferably from 2 to 8 µm.

The ink composition may also include plasticizers to increase the oxygen transmission rate, examples of plasticizers can include citroflex, dibutyl sebacate and sulphonamide plasticizers.

The present invention is further illustrated by the following non-limiting Examples.

EXAMPLE 1

Synthesis of polybutylacrylate-co-2-acrylamido-2-methyl propane sulphonic acid 4.16 g, (0.05 equivalents, 0.020 mol) of 2-acrylamido-2-methyl-1-propanesulphonic acid was dissolved in 62 g of 2-propanol while stirring under reflux under a positive pressure of nitrogen. 51.47 g (1 equivalent, 0.402 mol) of n-butyl acrylate was added portion wise under reflux, followed by 0.6 g of 1,1'-azobis-(cyclohexanecarbonitrile), and the reaction was allowed to reflux for 8 hours. The solvent was then removed under reduced pressure to give a clear viscous oil. Analysis by gel permeation chromatography (GPC) confirmed the average molecular weight to be 113200.

EXAMPLE 2

Ink Preparation & Printing 1.532 g of polybutylacrylate-co-2-acrylamido-2-methyl propane sulphonic acid (prepared as described in Example 1) was placed in a 50 ml jar containing a stirring bead. 4.8 g of isopropanol was added, and the mixture was stirred until the contents dissolved. 0.5 g of polydimethylsiloxane then was added, and the mixture was stirred until the contents dissolved to give a clear solution. 100 µl of 1N aqueous potassium Hydroxide was added, followed by 13.6 mg tris(4,7-diphenyl-1-10-phenanthroline)ruthenium (II) chloride. Stirring was continued for a further 4 hours to allow for the ion exchange process.

The ink solution of Example 2 was coated onto the corona-treated side of orientated polypropylene (OPP) with a K-bar number 2 with a wet film deposit thickness of 12 µm. The film was gently dried with a standard hair dryer for 30 seconds.

EXAMPLE 3

Oxygen Measurements

Oxygen sensitive coatings measurements were recorded using the OxySense 4000 measuring system with probe. The probe tip contains a blue LED light source with a wavelength of 400 nm. The manufacturer's instructions for calibration of the equipment and verification of the accuracy of readings were followed. After calibration, readings were taken in air, and in a zero oxygen environment (placing an ink film in a transparent plastic bag purged under a positive pressure of nitrogen).

Ink prepared as described in Example 2.
Oxygen measurement in air: 20.7%.
Oxygen measurement in nitrogen: 0.1%.

EXAMPLE 4

Ink Preparation & Printing 15.22 g of polybutylacrylate-co-2-acrylamido-2-methyl propane sulphonic acid (prepared as described in Example 1) was placed in a 50 ml jar. 38 g of isopropanol was added, and the mixture was placed on a ball jar mill model 12VS roller until the contents dissolved. 5 g of polydimethylsiloxane was added and further rolling was continued until the contents dissolved to give a clear solution. 300 µl of 1N aqueous potassium hydroxide was added, followed by 101 mg of tris(4,7-diphenyl-1-10-phenanthroline)ruthenium (II) chloride. After a further 4 hours on the ball jar mill model 12VS roller, the ink solution was ready for coating.

Viscosity measurement: 24.5 seconds with Zahn cup 2.

Ink measurements were taken as described in Example 2, and the ink was coated on to OPP with K-bar number 2, also as described in Example 2.

EXAMPLE 5

Oxygen Measurements

Carried out as in Example 3
Ink prepared as described in Example 4.
Oxygen measurement in air: 20.6%.
Oxygen measurement in nitrogen: 0.0%.

EXAMPLE 6

Ink Preparation & Printing 15.22 g of polybutylacrylate-co-2-acrylamido-2-methyl propane sulphonic acid (prepared as described in Example 1) was placed in 50 ml jar. 38 g of isopropanol was added and the mixture was placed on a ball jar mill model 12VS roller until the contents dissolved. 5 g of polydimethylsiloxane was added, and further rolling was continued until the contents dissolved to give a clear solution. 1.08 g of tetramethylammonium hydroxide in 0.5 g water was added, followed by 101 mg of tris(4,7-diphenyl-1-10-phenanthroline)ruthenium (II) chloride. After a further 4 hours on the ball jar mill model 12VS roller, the ink solution was ready for coating.

Viscosity measurement: 23.5 seconds with Zahn cup 2.

Ink measurements were taken as described in Example 2, and the ink was coated on to OPP with K-bar number 2, also as described in Example 2.

EXAMPLE 7

Oxygen Measurements

Carried out as in Example 3
Ink prepared as described in Example 6.
Oxygen measurement in air: 21.4%.
Oxygen measurement in nitrogen: 0.1%.

EXAMPLE 8

Testing of Oxygen Sensitive Ink Under Modified Atmosphere Packaging Applications Pouches were prepared from laminates comprising an outer layer of PET (Camclear) laminated with an interior layer of low density polyethylene (LDPE). The LDPE interior layer was coated with the oxygen sensitive ink (Pouch 1a. 2-3 µm thickness; Pouch 1b. 8-10 µm thickness. Each pouch was sealed using a MultiVac system (Model A 300/16) under an atmosphere of nitrogen and the interior oxygen content was measured. To confirm the accuracy and consistency of the oxygen measurements the interior of the pouch also contained an Oxydot®. Several readings were taken with the OxySense® measurement system; generally readings were consistent and similar to the Oxydot.

Pouch 1a. Oxygen sensor 2-3 µm thickness. Oxygen content: 0.1%.
Pouch 1a. Oxydot. Oxygen content: −0.1%.
Pouch 1b. Oxygen sensor 8-10 µthickness. Oxygen content: 0.0%.
Pouch 1b. Oxydot. Oxygen content: −0.1%.

EXAMPLE 9

Synthesis of Polybutylacrylate-Co-Ethylene Glycol Methacrylate Phosphate 6.14 g (0.05 equivalents, 0.029 mol) of ethylene glycol methacrylate phosphate was dissolved in 200 ml of methanol while stirring under reflux under a positive pressure of nitrogen. 75 g (1 equivalent, 0585 mol) of n-butyl acrylate was added portion wise under reflux, followed by 0.6 g of 1,1'-azobis-(cyclohexanecarbonate), and the reaction was allowed to reflux for 8 hours. The solvent was then removed under reduced pressure to give clear viscous oil.

EXAMPLE 10

Ink Preparation & Printing

Optimized Ink Formulation
4.1 g of polybutylacrylate-co-ethylene glycol methacrylate phosphate (prepared as described in Example 9) was placed in a 50 ml jar together with 10.2 g of R2013. 32.6 g of ethyl acetate and 1.5 g of ethanol were added and the mixture was placed on a ball jar mill model 12VS roller until the contents dissolved. 0.245 g of Cabosil TS610 and 0.435 g of cellulose acetate proprionate and 0.124 g of tris(4,7-diphenyl-1-10-phenanthroline)ruthenium (II) chloride. After a further 4 hours on the ball jar mill model 12VS roller, the ink solution was ready for coating.

Viscosity measurement: 23 seconds with Zahn cup 2.

Ink measurements were taken as described in Example 2, and the ink was coated on to OPP using a Saueressig gravure proofer (C.P. 90/60).

EXAMPLE 11

Oxygen Measurements

Carried out as Example 3.
Ink prepared as described in Example 10.
Oxygen measurement in air: 20.3%.
Oxygen measurement in nitrogen containing 2% oxygen: 2.03%

The invention claimed is:
1. An ink composition comprising:
a solvent;
an oxygen sensitive dye capable of fluorescing in a manner proportional to oxygen content; and
a polymer matrix for the dye, wherein the dye is immobilized in the polymer matrix, wherein the polymer matrix comprises units having pendant sulphonic acid groups or salts or esters of such groups, and wherein, the polymer matrix comprises:
(a) a copolymer of an acrylic monomer or oligomer and an ethylenically unsaturated compound containing one or more sulphonic groups; or
(b) a reaction product of a polymer containing pendant reactive groups with a sulphonic-group-containing compound of formula (VII) or (VIII):

$$HO-X^1-R^2-X^2-Z \quad (VII)$$

$$H_2N-X^1-R^2-X^2-Z \quad (VIII)$$

in which:
$R^1$ represents a hydrogen atom or a $C_1$-$C_6$ alkyl group;
$X^1$ represents an oxygen atom, a group of formula —NH— or an alkylene group;
$R^2$ represents an alkylene group, an arylene group, a group -A-B- (where one of A and B is an alkylene group and the other of A and B is an arylene group, an oxyalkylene group or an alkyleneoxy group);
$X^2$ represents an oxygen atom or an alkylene group; and
Z represents a group of formula (II)

$$-SO_3H \quad (II).$$

2. The composition of claim 1, in which the dye comprises ruthenium(II), osmium(II), iridium(III), rhodium(III) and chromium ions with a ligand.
3. The composition of claim 2, in which the ligand is an α-diimine ligand.
4. The composition of claim 3, in which the ligand is 2,2'-bipyridine, 1,10-phenanthroline, 4,7 diphenyl-1,10-phenanthroline, 4,7-disulphonated-diphenyl-1,10-phenanthroline, 5-bromo-1,10-phenanthroline, or 5-chloro-1,10-phenanthroline.
5. The composition of claim 4, in which the dye is a tris(2,2'-bipyridine)ruthenium(II) salt, a tris(1,10-phenanthroline)ruthenium(II) salt or a tris(4,7-diphenyl-1,10-phenanthroline)ruthenium (II) salt.
6. The composition of claim 4, in which the dye is a tris(4,7-diphenyl-1-10-phenanthroline)ruthenium (II) salt.

7. The composition of claim 1, in which the acrylic monomer is acrylic acid, methacrylic acid, a $C_1$-$C_6$ alkyl acrylate, a $C_1$-$C_6$ alkyl methacrylate, or an aryl or aralkyl acrylate or methacrylate.

8. The composition of claim 7, in which the ethylenically unsaturated compound containing a sulphonic group has the formula (V):

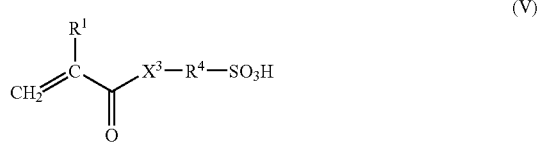

(V)

in which:
$R^1$ represents a hydrogen atom or a $C_1$-$C_6$ alkyl group;
$X^3$ represents an oxygen atom or a group of formula —NH—; and
$R^4$ represents an alkylene group, an arylene group, an oxyalkylene group or an alkyleneoxy group;
or is a salt or ester thereof.

9. The composition of claim 1, in which the sulphonic-group-containing compound is 3-hydroxy-1-propanesulphonic acid or 3-amino-1-propanesulphonic acid.

10. The composition of claim 1, formulated for flexogravure or inkjet printing.

11. The composition of claim 1, formulated for litho or letterpress printing.

12. A substrate printed or coated with a composition of claim 1.

13. The substrate of claim 12 in the form of a sealed pouch.

14. The composition of claim 4, in which the dye is a tris(4,7-diphenyl-1,10-phenanthroline)ruthenium (II) chloride salt.

15. The composition of claim 1, in which the sulphonic group containing compound is 2-acrylamido-2-methyl-1-propanesulphonic acid, 3-sulphopropyl acrylate potassium salt, or 3-sulphopropyl methacrylate potassium salt.

* * * * *